(12) United States Patent
Arakawa et al.

(10) Patent No.: US 6,664,462 B2
(45) Date of Patent: Dec. 16, 2003

(54) METAL COMPLEX HAVING β-DIKETONATE, PROCESS FOR PRODUCTION THEREOF, PHOTOELECTRIC CONVERSION ELEMENT, AND PHOTOCHEMICAL CELL

(75) Inventors: Hironori Arakawa, Tsukuba (JP); Hideki Sugihara, Tsukuba (JP); Kohjiro Hara, Tsukuba (JP); Yoshiaki Takahashi, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 09/959,949

(22) PCT Filed: Dec. 26, 2000

(86) PCT No.: PCT/JP00/09254
§ 371 (c)(1),
(2), (4) Date: Nov. 13, 2001

(87) PCT Pub. No.: WO01/68608
PCT Pub. Date: Sep. 20, 2001

(65) Prior Publication Data
US 2002/0170594 A1 Nov. 21, 2002

(30) Foreign Application Priority Data
Mar. 13, 2000 (JP) .................................. 2000-069517

(51) Int. Cl.[7] ............ C07D 213/79; C07D 471/04; H01M 14/00; C07F 15/00; C07C 49/92
(52) U.S. Cl. ................ 136/263; 136/252; 136/256; 257/40; 257/43; 257/431; 546/2; 546/10; 502/161; 556/16; 556/1; 556/32; 987/16; 987/304; 429/111
(58) Field of Search ............... 136/263, 252, 136/256; 257/40, 43, 431; 429/111; 546/2, 10; 502/161; 556/16, 1, 32; 987/16, 304

(56) References Cited
U.S. PATENT DOCUMENTS
3,647,832 A * 3/1972 Chabardes et al. ........... 546/2

FOREIGN PATENT DOCUMENTS
EP         887 817 A2      12/1998
EP         A2 887 817      12/1998
EP         1049117 A2 *    11/2000

(List continued on next page.)

OTHER PUBLICATIONS
Dwyer et al, Aust. J. Chem., vol. 16, (1963) pp. 544–548.*
Bryant et al, Aust. J. Chem., vol. 24 (1971), pp. 257–273.*

(List continued on next page.)

Primary Examiner—Alan Diamond
(74) Attorney, Agent, or Firm—Birch, Stewart, Kolasch & Birch, LLP

(57) ABSTRACT

A metal complex having a β-diketonate represented by the following formula (1):

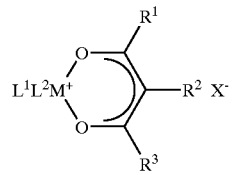

wherein M represents a metal atom of the VIII group, $R^1$, $R^2$ and $R^3$ represent a group or an atom selected from the group consisting of an alkyl group, an aryl group, a hydroxyl group, an amino group, an alkoxy group, a hydrogen atom and a halogen atom; $X^{-1}$ represents an ion selected from a halogen, nitric acid, sulfonic acid, fluoroboric acid, fluorophosphoric acid, or perchloric acid ion; $L^1$ or $L^2$ represents a 2,2'-bipyridine or 1,10-phenanthroline group where these groups may be substituted with a group or an atom selected from an alkyl group, a carboxyl group, a sulfonic acid group, a phosphonic acid group, a hydroxyl group, an amino group, a hydrogen atom and a halogen atom. A photoelectric conversion element and a photochemical cell using the above-mentioned metal complex.

12 Claims, 1 Drawing Sheet

LIGHT

FOREIGN PATENT DOCUMENTS

| | | | |
|---|---|---|---|
| GB | 956242 | * | 4/1964 |
| JP | 1-220380 | | 9/1989 |
| JP | 8-99041 | | 4/1996 |
| JP | 11-144772 | | 5/1999 |
| JP | A11-167937 | | 6/1999 |
| JP | 11-167937 | | 6/1999 |
| JP | 11-273753 | | 10/1999 |
| JP | A11-273753 | | 10/1999 |
| JP | A2000-106223 | | 4/2000 |
| JP | 2000-106223 | | 4/2000 |
| WO | WO 94/04497 | | 3/1994 |

OTHER PUBLICATIONS

Uddin et al, Structural Chemistry, vol. 8, No. 2, (1997), pp. 131–139.*

Uddin et al, Z., anorg. allg. Chem., 624 (1998) pp. 1699–1705.*

Takahashi et al, Inorganica Chimica Acta, 310(2), pp. 169–174, Dec. 15, 2000.*

* cited by examiner

LIGHT

METAL COMPLEX HAVING β-DIKETONATE, PROCESS FOR PRODUCTION THEREOF, PHOTOELECTRIC CONVERSION ELEMENT, AND PHOTOCHEMICAL CELL

This application is the national phase under 35 U.S.C. §371 of PCT International Application No. PCT/JP00/09254 which has an International filing date of Dec. 26, 2000, which designated the United States of America.

TECHNICAL FIELD

The present invention relates to a metal complex having a β-diketonate, a process for producing the same, a photoelectric conversion element, and a photochemical cell.

BACKGROUND ART

Inorganic semiconductors, such as a monocrystal, polycrystal, and amorphous silicon, are used as photoelectric conversion materials used for solar cells. These materials are pointed out to have the problems that they require large energy in a production process and contain components that are not environmentally preferable. To deal with these problems, an energy converter utilizing a photoelectric chemical reaction that takes place at the boundary between a photo-semiconductor and an electrolytic solution, has been developed. Titanium oxide used in the device is stable photoelectrochemically, and superior as an electrode material of a metal oxide semiconductor. However, titanium oxide has an inferior spectrum matching sunlight, and it is not expected to have high efficiency, because it has a bandgap as large as 3.0 eV.

Therefore, an organic dye is utilized to be adsorbed onto the surface of titanium oxide, to sensitize it. It is known that the adsorbed dye has a sensitizing effect, and that titanium dioxide which has a large specific surface area as the electrode of a photo-semiconductor, is used to improve the efficiency of utilization of light (JP-A-1-220380 ("JP-A" means unexamined published Japanese patent application.)). Also, it is known to use a thin film of titanium dioxide having micropores on the surface thereof (JP-A-8-99041). However, titanium dioxide has a large forbidden band and therefore cannot absorb light in the visible region. It is therefore necessary to coat titanium dioxide with a photo-sensitizer that absorbs light in a wavelength range in 300 to 2000 nm, to aim at sunlight, and an organic dye is used for this purpose.

As the organic dye, many compounds, such as xanthene-series dyes, cyanine-series dyes, basic dyes, porphyrin-series compounds, azo dyes, and Ru complexes, are known (JP-A-11-144772 and JP-T-7-500630 ("JP-T" means a publication of the translation of an international patent application.)). It has been considered that a solar cell, which is coated with an Ru complex and is sensitized with a dye, has a high photoelectric conversion efficiency, and that such the solar cell is produced at lower costs in contrast to even a silicon solar cell. Although these points are advantageous, the performance of a cell depends on a sensitizing dye, and it is desired to develop a high-performance dye upon developing a high-performance cell.

An object of the present invention is to provide a dye having high light absorbance over a wide wavelength range. Another object of the present invention is to provide a photoelectric conversion element using the dye. A further object of the present invention is to provide a photochemical cell using the element.

Other and further objects, features, and advantages of the invention will appear more fully from the following description, taken in connection with the accompanying drawings.

DISCLOSURE OF THE INVENTION

The inventors of the present invention, having made earnest studies on the above objects, developed a dye which is composed of a novel β-diketonate metal complex and found that light in a wide wavelength range (less than 800 nm) can be absorbed by this dye, to complete the present invention.

Accordingly, according to the present invention the following inventions are provided.

(1) A metal complex having a β-diketonate represented by the following formula (1):

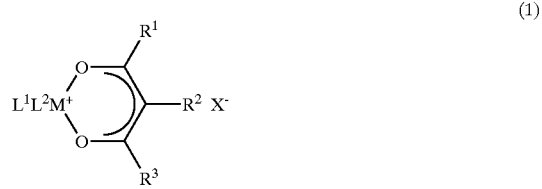

(1)

wherein M represents a metal atom of the VIII group; $R^1$, $R^2$ and $R^3$ each represent a group or an atom select the group consisting of an alkyl group, an aryl gr hydroxyl group, an amino group, an alkoxy group, a hydrogen atom and a halogen atom; $X^{-1}$ represents an ion selected from a halogen ion, a nitric acid ion, a sulfonic acid ion, a fluoroboric acid ion, a fluorophosphoric acid ion and a perchloric acid ion; and $L^1$ or $L^2$ respectively represents a 2,2'-bipyridine group or a 1,10-phenanthroline group, each of which may be substituted with a group or an atom selected from an alkyl group, a carboxyl group, a sulfonic acid group, a phosphonic acid group, a hydroxyl group, an amino group, a hydrogen atom and a halogen atom.

(2) A metal complex having a β-diketonate represented by the following formula (2):

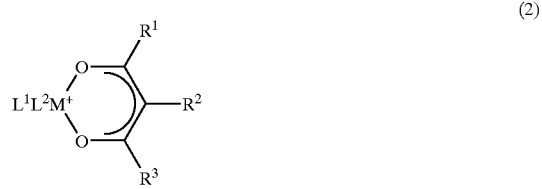

(2)

wherein M represents a metal atom of the VIII group; $R^1$, $R^2$ and $R^3$ each represent a group or an atom selected from the group consisting of an alkyl group, an aryl group, a hydroxyl group, an amino group, an alkoxy group, a hydrogen atom and a halogen atom; and $L^1$ or $L^2$ respectively represents a 2,2'-bipyridine group or a 1,10-phenanthroline group, in which one or both of $L^1$ or $L^2$ may be substituted with an acidic group selected from a carboxyl group, a sulfonic acid group, a phosphonic acid group and a hydroxyl group each of which is neutralized.

(3) A method for producing a metal complex having a β-diketonate represented by the following formula (1), comprising heating a metal complex of the VIII group having, as a ligand, $L^1$ $L^2$ which represent a 2,2'-bipyridine group or a 1,10-phenanthroline group (these groups may be substituted with a group or an atom selected from an alkyl group, a carboxyl group, a sulfonic acid group, a phosphonic acid group, a hydroxyl group, an amino group, a hydrogen atom and a halogen atom), and a β-diketone derivative, in the presence of an alkali and a solvent, and treating the resulting product with an aqueous solution containing an acid.

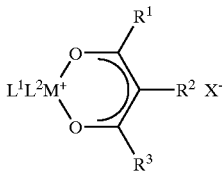

(1)

(4) A method for producing a metal complex having a βdiketonate represented by the following formula (2), comprising adding an alkali to the aqueous solution containing the β-diketonate described in the above item (3).

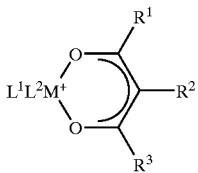

(2)

(5) A photoelectric conversion element, which comprises a porous oxide semiconductor layer laminated on a layer composed of an electric conductor, and the metal complex as stated in the above item (1) or (2) adsorbed to the porous oxide semiconductor layer.

(6) A photochemical cell, which comprises the photoelectric conversion element as stated in the above item (5), a counter electrode, and a charge-transfer layer.

BEST MODE FOR CARRYING OUT THE INVENTION

Figure 1:
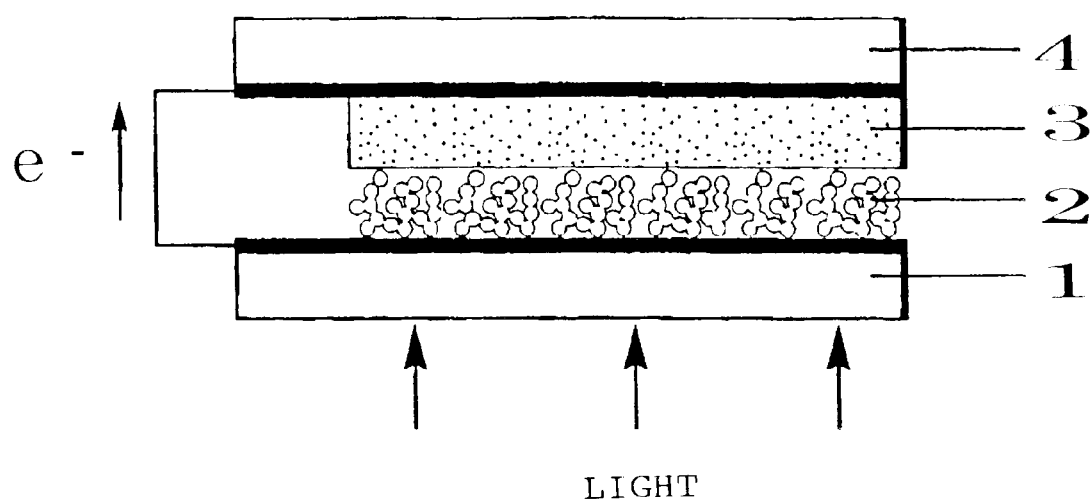
FIG. 1 is a schematic view showing the layer structure of a preferred photochemical cell according to the present invention.

The present invention will be further explained hereinafter.

A novel metal complex of the present invention is a metal complex having the following structure and two types of β-diketonate.

(1) A metal complex having a β-diketonate represented by the following formula (1):

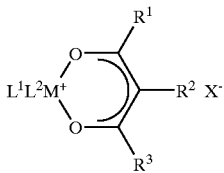

(1)

wherein M represents a metal atom of the VIII group, $R^1$, $R^2$ and $R^3$ represent groups or atoms selected from the group consisting of an alkyl group, an aryl group, a hydroxyl group, an amino group, an alkoxy group, a hydrogen atom and a halogen atom, $X^{-1}$ represents an ion selected from a halogen ion, a nitric acid ion, a sulfonic acid ion, a fluoroboric acid ion, a fluorophosphoric acid ion and a perchloric acid ion and $L^1$ or $L^2$ respectively represents a 2,2'-bipyridine group or a 1,10-phenanthroline group where these groups may be substituted with a group or an atom selected from an alkyl group, a carboxyl group, a sulfonic acid group, a phosphonic acid group, a hydroxyl group, an amino group, a hydrogen atom and a halogen atom.

(2) A metal complex having a β-diketonate represented by the following formula (2):

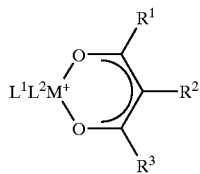

(2)

wherein M represents a metal atom of the VIII group, $R^1$, $R^2$ and $R^3$ represent groups or atoms selected from the group consisting of an alkyl group, an aryl group, a hydroxyl group, an amino group, an alkoxy group, a hydrogen atom and a halogen atom, and $L^1$ or $L^2$ respectively represents a 2,2'-bipyridine group or a 1,10-phenanthroline group where one or both of $L^1$ or $L^2$ may be substituted with an acid group selected from a carboxyl group, a sulfonic acid group, a phosphonic acid group and a hydroxyl group which are neutralized.

The above-mentioned compounds will be explained in more detail.

The metal of the above metal complex is a metal of the VIII group. Metals of the VIII group include elements of iron, cobalt, nickel, ruthenium, rhodium, palladium, osmium, iridium and platinum. As the metal of the metal complex, a metal which is properly selected from these VIII group metals may be used.

$R^1$, $R^2$ and $R^3$ are groups or atoms selected from alkyl groups, aryl groups, hydroxyl groups, amino groups, aminoalkyl groups in which a part of amino group is substituted with an alkyl group), alkoxy groups, a hydrogen atom and halogen atoms. The alkyl group is an aliphatic saturated hydrocarbon group which may have a straight-chain or branched chain. Given as specific examples of the alkyl group are a methyl group, ethyl group, propyl group, i-propyl group and groups of n-butyl, i-butyl, sec-butyl and tert-butyl. The number of the carbons of the alkyl group may be optionally selected as far as it does not disturb the production of a metal complex. As to the number of carbons in the alkyl group, alkyl groups whose carbon number is in a range from 1 to 10 are generally selected. The aryl group represents a group obtained by removing one hydrogen atom from an aromatic hydrocarbon, specifically, a phenyl group, a group such as a tolyl group and xylyl group in which a phenyl group may be substituted with an alkyl group such as a methyl group or ethyl group, biphenyl group, naphthyl group, anthryl group, phenanthryl group. The alkoxy group is a group in which oxygen is bonded to an alkyl group and specific examples of the alkoxy group may include a methoxy group, ethoxy group, propoxy group, butoxy group, pentyloxy group and hexyloxy group. Specific examples of the halogen atom may include chlorine, fluorine, bromine and iodine.

$X^{-1}$ represents a negative monovalent ion. The halogen ion is specifically an ion of a halogen atom selected from chlorine, fluorine, bromine and iodine.

$L^1$ or $L^2$ respectively represent a 2,2'-bipyridine group

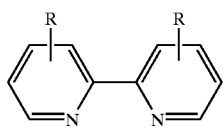

or a 1,10-phenanthroline group.

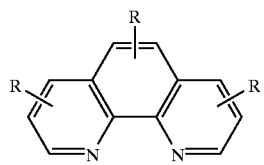

These groups may be substituted with a substituent R. The substituent R may be substituted with a group or atom selected from an alkyl group (those having 1 to 10 carbon atoms and a straight chain or branched chain), carboxyl group, sulfonic acid group, phosphonic acid group, hydroxyl group, amino group, hydrogen atom and halogen atom. The substituent R may be substituted not only with one substituent but also with two or more substituents.

The structural formula of the β-diketonate as the ligand is specifically shown as follows.

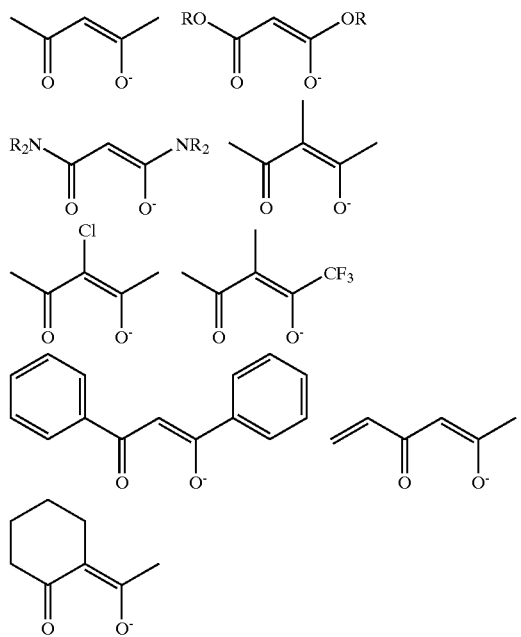

In the above formulae, R has the same meaning as defined in $R^1$, $R^2$ or $R^3$ of the above-mentioned β-diketonate.

Specific examples of the structural formula of the metal complex having the β-diketonate represented by the mentioned formula (1), are shown below.

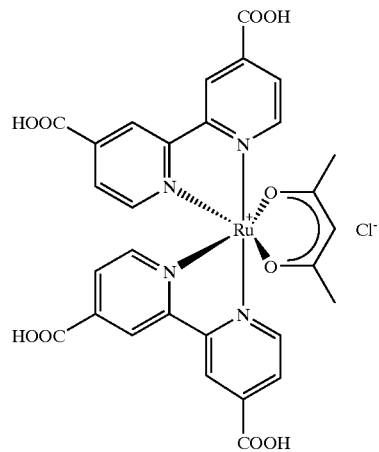

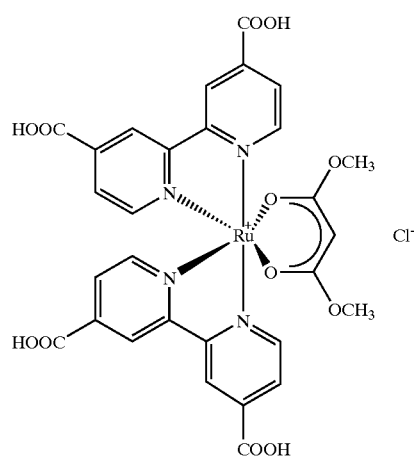

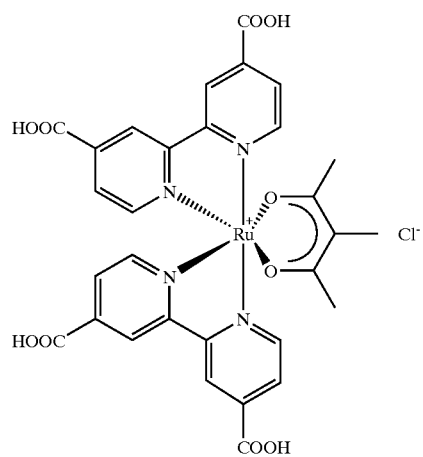

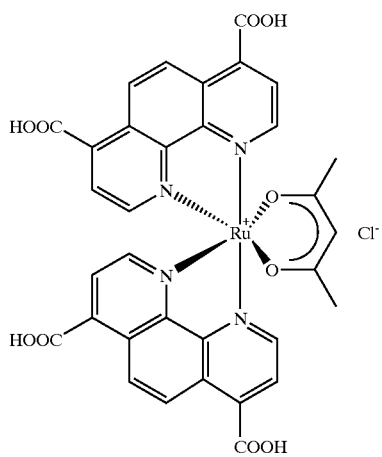
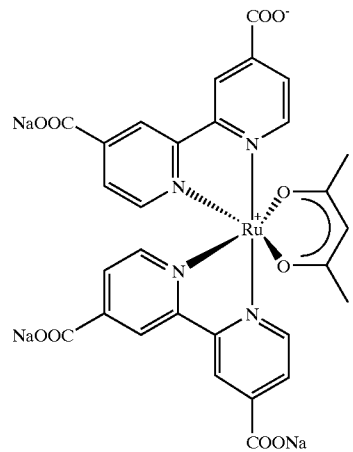
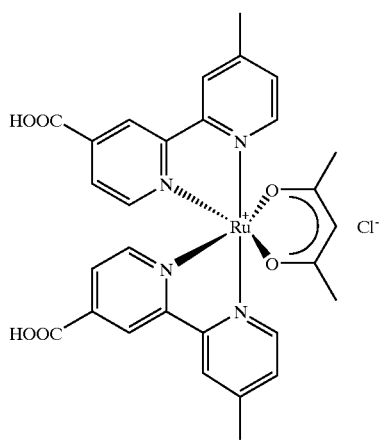
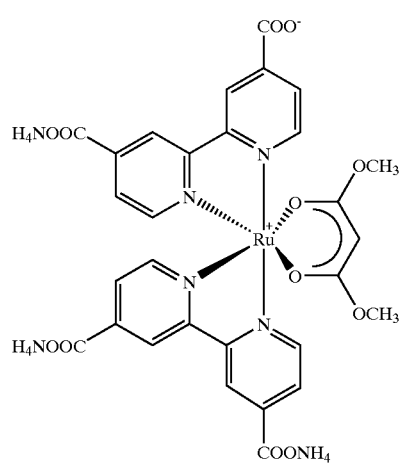
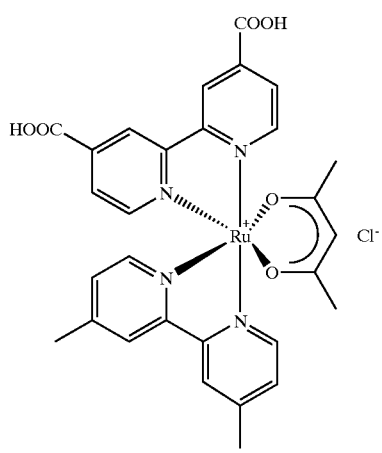
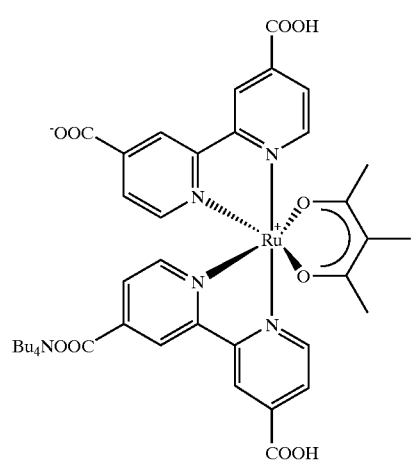
Specific structural formulas of the metal complex having the β-diketonate represented by the above-mentioned formula (2), are shown below.

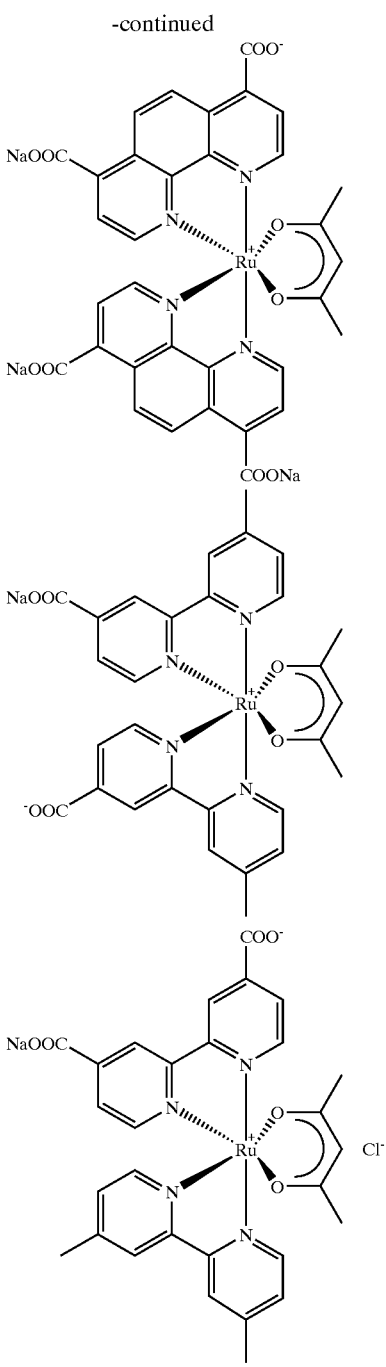

A process for producing the metal complex having a β-diketonate represented by the above formula (1) is explained below. A process for producing a metal complex having a β-diketonate shown by the following formula (1), the process comprising heating a metal complex of the VIII group having, as a ligand, $L^1$ $L^2$ which represent a 2,2′-bipyridine group or a 1,10-phenanthroline group (these groups may be substituted with a group or an atom selected from an alkyl group, a carboxyl group, a sulfonic acid group, a phosphonic acid group, a hydroxyl group, an amino group, a hydrogen atom and a halogen atom) and a β-diketone derivative in the presence of an alkali and a solvent, and then treating the resulting product with an aqueous solution containing an acid.

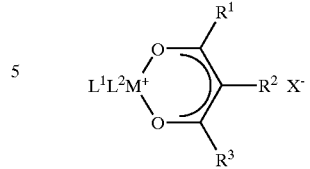

(1)

The raw material is a metal complex of the VIII group having, as a ligand, a group containing $L^1$ $L^2$ which represent a 2,2′-bipyridine group or a 1,10-phenanthroline group (these groups may be substituted with a group or an atom selected from an alkyl group, a carboxyl group, a sulfonic acid group, a phosphonic acid group, a hydroxyl group, an amino group, a hydrogen atom and a halogen atom), and a β-diketone or its derivative. All these compounds are known compounds.

As the metal, ruthenium, iron, cobalt, nickel, palladium or platinum can be used. Examples of the β-diketone may include acetylacetone.

As examples of the β-diketone derivative, the following compounds may be given.

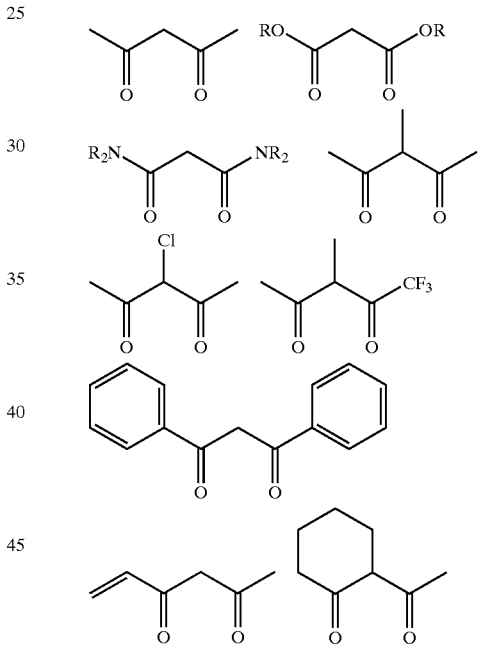

In the above formulae, R has the same meaning as defined in $R^1$, $R^2$ or $R^3$ of the above-mentioned β-diketonate.

The solvent may be any one of those which can solubilize the metal complex and specific examples of the solvent may include water, a mixture of dimethylformamide and water and alcohol.

The alkali is used to generate the β-diketonate which is an anionic type and, specifically, sodium carbonate, sodium hydroxide, sodium alkoxide or the like can be used as the alkali. The acid used in the above reaction serves to neutralize the reaction system and to add an ion X to the complex obtained. X is a group selected from a halide ion, nitric acid ion, sulfonic acid ion, fluoroboric acid ion, fluorophosphoric acid ion and perchloric acid ion. The acid is acids having these Xs. Specific examples of the acid may include hydrochloric acid, hydrofluoric acid, hydrobromic acid, nitric acid, trifluoromethanesulfonic acid, toluene sulfonic acid, tetrafluoroboric acid, hexafluorophosphoric acid and perchloric acid.

It is effective to carry out the heating in reflux condition.

The reaction scheme is shown as follows.

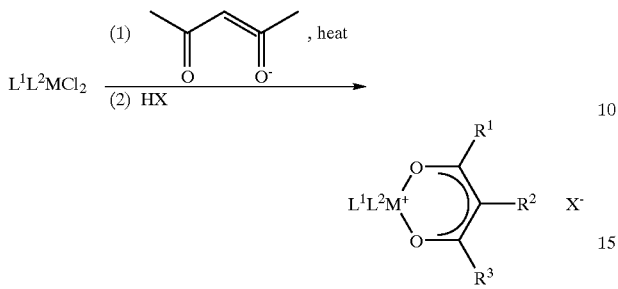

For example, when the object product to be obtained is a ruthenium metal complex, its ligand $L^1$ $L^2$ as is 2,2'-bipyridine-4,4'-dicarboxylic acid, $R^1$ and $R^3$ are methyl groups, $R^2$ is a hydrogen atom and $X^-$ is a perchloric acid ion, the ruthenium metal complex is produced as follows.

As the VIII group metal complex, cis-dichlorobis(2,2'-bipyridine-4,4'-dicarboxylic acid) ruthenium is used and as the β-diketone, acetylacetone is used.

A metal complex cis-dichlorobis(2,2'-bipyridine-4,4'-dicarboxylic acid) ruthenium is dissolved in a solvent to use. As the solvent, any one of those which can dissolve the above-mentioned VIII group metal complex can be optionally used. Specifically, a mixed solvent of dimethylformamide and water etc. can be used. As the alkali, any one of those which can produce the β-diketonate can be optionally utilized. Specific examples of the alkali may include sodium carbonate.

Heating is required for the reaction and therefore the raw materials are heated under reflux.

The product obtained with the above-mentioned treatments is dried, and an aqueous perchloric acid solution which is an aqueous solution containing $X^-$ is added to the dried product to run a reaction. After that, when the reaction mixture is put in an acidic condition, a precipitate is produced. The precipitate is separated by filtration and washed with methanol, followed by drying, and the object product can be obtained.

The above reaction is shown as follows.

For the production of the metal complex having the β-diketonate as shown in the above-described formula (2), the metal complex containing the β-diketonate represented by the above-described formula (1) is produced and the resulting compound is treated by a base to produce the metal complex. As specific examples of the base, sodium hydroxide and ammonia may be given. Additionally, the product obtained in the stage prior to the treatment using the aqueous solution containing $X^-$ can be used.

The photoelectric conversion element of the present invention is formed with forming an oxide semiconductor layer on a conductive substrate which is composed of a conductive material and adsorbing the above-mentioned metal complex having the β-diketonate of the present invention to the oxide semiconductor layer.

As the conductive material, a metal, carbon, conductive polymer or conductive glass can be used. These materials can be used whether they are light-transmittable or not. Generally, as to the transmittance, conductive materials having a light-transmittance of 80% or more are preferably used in general. Conductive materials having a plate-like form or a sheet-like form can be used. These materials act as a support. In the case of using conductive glass, a film of a conductive metal oxide made of tin oxide or indium/tin complex oxide can be formed on the surface of glass to use. Further, a conductive layer of a metal or carbon may be formed on conductive substrate to use. It is preferable that the surface resistance of the conductive substrate is generally a value of 10 Ω/cm² or less.

In case that the oxide semiconductor layer formed on the surface of the above-mentioned conductive material is formed, a dispersion solution in which a fine particle of the oxide semiconductor is dispersed in a solvent is produced, and this dispersion solution is allowed to adhered to the surface of the conductive material, followed by baking, to form a thin film composed of the oxide semiconductor.

As the oxide semiconductor to be used, an oxide of a transition metal such as titanium, niobium, zinc, tin, zirconium, yttrium, lanthanum or tantalum is used. Perovskite type oxides such as strontium titanate and calcium titanate can be also used. These semiconductors bring about very preferable results.

The finer the primary particle diameter of these semiconductor oxides is, the more preferable results are brought about.

The particle diameter is in a range from generally 1 to 5000 nm and preferably 2 to 50 nm.

As the solvent used to disperse this fine particulate-like semiconductor oxide in the solvent, any one of solvents which can be dispersed each of these oxide semiconductors can be optionally used. As the solvent, a solvent selected from water, an organic solvent, and water and an organic solvent can be used. As the organic solvent, a hydrocarbon, alcohol, ether, ketone, ester or the like can be used.

In order to better the dispersion of the semiconductor oxide, various surfactants and a viscosity modifier can be used. As specific examples of the viscosity modifier, polyethylene glycol can be given.

The oxide semiconductor layer is baked in the presence of air in the condition of a temperature of 1000° C. or less. A temperature range between generally 300 and 800° C. and preferably 400 and 600° C. is adopted.

As the layer which is composed of the oxide semiconductor, a layer which has about 5 to 100 μm as thickness after baked is required. The oxide semiconductor layer obtained in this manner form a fine porous layer.

The oxide semiconductor layer formed on the above-mentioned conductive substrate is immersed in the dye dissolved in a solvent, so that a dye composed of the above-mentioned metal complex having the β-diketonate in the present invention is allowed to adsorb to the semiconductor oxide layer. As the solvent for the dye, methanol, acetonitrile, dimethylformamide, water or the like can be used. The concentration of the dye in the solvent is appropriately selected from the range from $10^{-5}$ to $10^{-2}$ M to use. An optimum concentration differs depending upon the type of dye. The immersing time is in a range from generally 0.5 to 24 hours and is appropriately selected within the order of this range according to the need.

As the immersing temperature, a temperature ranging from room temperature to 100° C. is appropriately selected in general.

The photocell of the present invention will be explained with reference to FIG. 1.

The photocell is composed of a counter electrode formed on the surface of a conductive substrate 1, and it is further constituted by a layer structure thereon comprising a thin film layer composed of a dye-carrying oxide semiconductor film 2, which is formed by absorbing a dye to an oxide semiconductor, a charge-transfer layer 3, and a counter electrode 4.

As the counter electrode, one obtained by forming a thin layer of platinum, rhodium, ruthenium, ruthenium oxide or carbon etc. on a conductive material or a conductive substrate is used.

As the charge transfer layer, a layer formed with an electrolytic solution containing a redox material in an organic solvent is used. As the redox material, a combination of, for example, $I^-/I_3^-$, $Br^-/Br_3^-$, $Fe^{2+}/Fe^{3+}$, $Sn^{2+}/Sn^{4+}$, $Cr^{2+}/Cr^{3+}$, $V^{2+}/V^{3+}$ or quinone/hydroquinone is used.

As specific examples of the organic solvent, acetonitrile, propionitrile, ethylene carbonate and propylene carbonate may be given. As this charge transfer layer, a gel electrolyte obtained by solidifying the electrolytic solution of the liquid charge-transfer layer which is composed of the above-mentioned electrolytic solution, or a solid high-molecular electrolyte containing a redox substance in a high molecular substance can be used.

The metal complex which is obtained according to the present invention and has the β-diketonate as a ligand is a dye which is composed of a metal complex exhibiting high light absorbance in the visible radiation region. Utilizing this characteristic, a photoelectric conversion element which makes use of visible rays can be obtained. The photochemical cell using this photoelectric conversion element exhibits a high photoelectric conversion efficiency.

EXAMPLES

The present invention will be described in more detail based on the examples given below, but the present invention is not meant to be limited by these examples.

Example 1

73 mg of cis-dichlorobis(2,2'-bipyridine-4,4'-dicarboxylic acid)ruthenium was dissolved in 15 ml of a solvent consisting of dimethylformamide and water (2:1). 203 mg of sodium carbonate was further added to the mixture, which was then stirred sufficiently. 0.10 ml of acetylacetone was added to the mixture and the resulting mixture was heated under refluxing over 3 hours. The resulting mixture containing the reaction product was dried by evaporation. A small amount of water was added and then an aqueous solution of dilute perchloric acid was added to the dried mixture to obtain an acidic solution.

After the solution was allowed to stand, the produced precipitate was separated by filtration, washed with methanol and dried to obtain 49 mg of a target ruthenium complex containing a β-diketonate.

The product obtained according to the above-mentioned manner was analyzed in terms of elemental analysis, mass spectrometry, NMR and measurements of infrared and visible-ultraviolet absorption and as a result, it was confirmed that the product had the following structural formula. M was a ruthenium metal, $L^1$ and $L^2$ were both 2,2'-bipyridine-4,4'-dicarboxylic acids, $R^1$ and $R^3$ were methyl groups, $R^2$ was a hydrogen atom and $X^-$ was a perchloric acid ion.

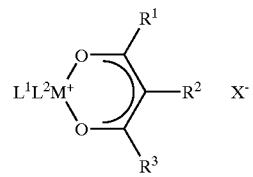

Example 2

The product obtained in the above Example 1 was suspended in water, to which was then added an aqueous concentrated ammonia solution. The resulting solution was dried to obtain a target ruthenium complex containing a β-diketonate.

The product obtained according to the above-mentioned manner was analyzed in terms of elemental analysis, mass spectrometry, NMR and measurements of infrared and visible-ultraviolet absorption and as a result, it was confirmed that the product had the following structural formula. M was a ruthenium metal, L1 and L2 were both ammonium-2,2'-bipyridine-4,4'-dicarboxylic acids, $R^1$ and $R^3$ were methyl groups and $R^2$ was a hydrogen atom.

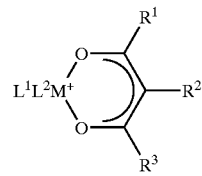

Example 3

Production of a Photoelectric Conversion Element 12 g of titanium oxide (P-25, manufactured by Nippon Aerosil Co., Ltd., surface area: 55 m²/g, average primary particle diameter: 50 nm or less) was added to 0.4 ml of acetylacetone, 20 ml of water and 0.2 ml of a dispersant (Triton X-100, manufactured by Aldrich) to prepare a dispersion solution. This dispersion solution was applied to a conductive glass substrate ($SnO_2$, 10 $\Omega/cm^2$) of 1 mm in thickness and baked in air under the condition of 500° C. for one hour. The resulting thin film of titanium oxide was immersed at room temperature for 12 hours, in a solution containing the β-diketonate ruthenium complex obtained in Example 1 in a concentration of 1 mM.

Example 4

Production of a Photochemical Cell

One counter electrode produced by vapor depositing platinum, a semiconductor thin film as produced in the above-mentioned Example 3, an acetonitrile solution layer containing iodine (0.1 M) and lithium iodide (0.5 M) as a charge layer and further another counter electrode were disposed on a conductive glass substrate ($SnO_2$, 10 $\Omega/cm^2$), to produce a photochemical cell.

The photochemical cell thus obtained was irradiated with pseudo sun light (1,000 $w/m^2$) using a solar simulator (manufactured by WACOM Co., Ltd.) to obtain a photocurrent of 13.2 $mA/cm^2$, a photovoltage of 0.74 V and a photoelectric conversion efficiency of 6.0%.

INDUSTRIAL APPLICABILITY

The metal complex containing the β-diketonate as a ligand which is obtained according to the present invention is a dye which is composed of a metal complex exhibiting high light absorbance in the visible radiation region and is therefore a suitable material to obtain a photoelectric conversion element utilizing visible rays by making use of these characteristics. A photochemical cell using this photoelectric conversion element exhibits a high photoelectric conversion efficiency.

Having described our invention as related to the present embodiments, it is our intention that the invention not be limited by any of the details of the description, unless otherwise specified, but rather be construed broadly within its spirit and scope as set out in the accompanying claims.

What is claimed is:

1. A metal complex having a β-diketonate represented by the following formula (1)

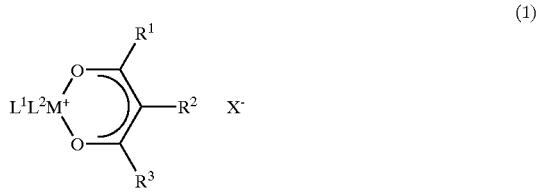

wherein M represents a metal atom of the VIII group; $R^1$, $R^2$ and $R^3$ each represent a group or an atom selected from the group consisting of an alkyl group, an aryl group, a hydroxyl group, an amino group, an alkoxy group, a hydrogen atom and a halogen atom; $X^-$ represents an ion selected from a halogen ion, a nitric acid ion, a sulfonic acid ion, a fluoroboric acid ion, a fluorophosphoric acid ion and a perchloric acid ion; and $L^1$ and $L^2$ represent a 2,2'-bipyridine group or a 1,10-phenanthroline group, each of which is substituted with at least one group or one atom selected from a carboxyl group, a sulfonic acid group, a phosphonic acid group, a hydroxyl group, an amino group, and a halogen atom.

2. A metal complex having a β-diketonate represented by the following formula (2):

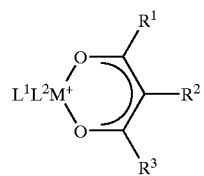

wherein M represents a metal atom of the VIII group; $R^1$, $R^2$ and $R^3$ each represent a group or an atom selected from the group consisting of an alkyl group, an aryl group, a hydroxyl group, an amino group, an alkoxy group, a hydrogen atom and a halogen atom; and $L^1$ and $L^2$ represent a 2,2'-bipyridine group or a 1,10-phenanthroline group, in which one or both of $L^1$ and $L^2$ is substituted with an acidic group selected from a carboxyl group, a sulfonic acid group, a phosphonic acid group and a hydroxyl group each of which is neutralized.

3. A method for producing a metal complex having a β-diketonate represented by the formula (1),

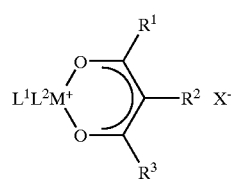

comprising heating a metal complex of the VIII group having, as ligands, $L^1$ and $L^2$ which represent a 2,2'-bipyridine group or a 1,10-phenanthroline group, each of which is substituted with at least one group or one atom selected from a carboxyl group, a sulfonic acid group, a phosphonic acid group, a hydroxyl group, an amino group, and a halogen atom, wherein M represents a metal atom of the VIII group; $R^1$, $R^2$ and $R^3$ each represent a group or an atom selected from the group consisting of an alkyl group, an aryl group, a hydroxyl group, an amino group, an alkoxy group, a hydrogen atom and a halogen atom;

and a β-diketonate derivative, in the presence of an alkali and a solvent, and treating the resulting product with an aqueous solution containing an acid such that $X^-$ represents an ion selected from the group consisting of a halogen ion, a nitric acid ion, a sulfonic acid ion, a fluoroboric acid ion, a fluorophosphoric acid ion, and a perchloric acid ion.

4. A method for producing a metal complex having a β-diketonate represented by the formula (2),

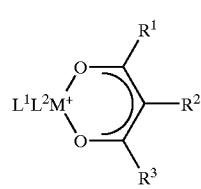

further comprising adding an alkali to the aqueous solution containing the β-diketonate described in claim 3.

5. A photoelectric conversion element, which comprises a porous oxide semiconductor layer laminated on a layer composed of an electric conductor, and the metal complex as claimed in claim 1 or 2 adsorbed to the porous oxide semiconductor layer.

6. A photochemical cell, which comprises the photoelectric conversion element as claimed in claim 5, a counter electrode, and a charge-transfer layer.

7. The metal complex of claim 1, wherein M is selected from the group consisting of iron, cobalt, ruthenium, rhodium, palladium, osmium, iridium, and platinum.

8. The metal complex of claim 1, wherein $X^-$ is an ion selected from the group consisting of a halogen ion, a nitric acid ion, a sulfonic acid ion, a fluoroboric acid ion, and a fluorophosphoric acid ion.

9. The metal complex of claim 2, wherein M is selected from the group consisting of iron, cobalt, ruthenium, rhodium, palladium, osmium, iridium, and platinum.

10. The method of claim 3, wherein the β-diketonate derivative is selected from the group consisting of

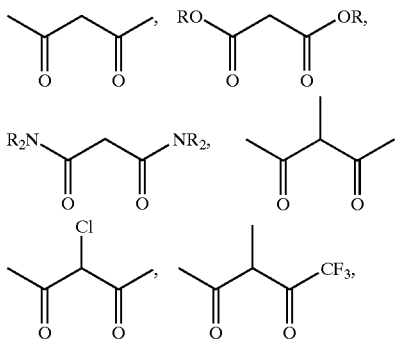

-continued

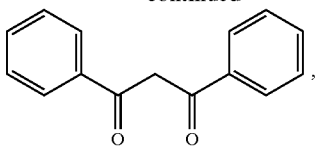

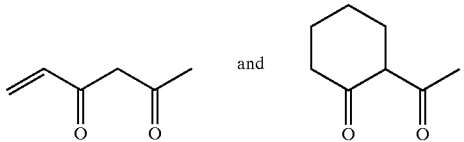

wherein R is an alkyl group or a hydrogen atom.

11. The method of claim 3, wherein the acid is selected from the group consisting of hydrochloric acid, hydrofluoric acid, hydrobromic acid, nitric acid, trifluoromethanesulfonic acid, toluenesulfonic acid, tetrafluoroboric acid, hexafluorophosphoric acid, and perchloric acid.

12. The method of claim 3, wherein the acid is hydrochloric acid, hydrofluoric acid, hydrobromic acid, nitric acid, trifluoromethanesulfonic acid, toluenesulfonic acid, tetrafluoroboric acid, or hexafluorophosphoric acid.

* * * * *